US009423120B2

(12) United States Patent
Fang

(10) Patent No.: US 9,423,120 B2
(45) Date of Patent: Aug. 23, 2016

(54) LED CANDLE LAMP HAVING HUMIDIFYING AND FLAVORING FUNCTION

(71) Applicant: Jian Fang, Guangdong Province (CN)

(72) Inventor: Jian Fang, Guangdong Province (CN)

(*) Notice: Subject to any disclaimer, the term of this patent is extended or adjusted under 35 U.S.C. 154(b) by 164 days.

(21) Appl. No.: 14/314,016

(22) Filed: Jun. 24, 2014

(65) Prior Publication Data

US 2015/0338087 A1    Nov. 26, 2015

(30) Foreign Application Priority Data

May 22, 2014   (CN) ...................... 2014 2 0265280 U

(51) Int. Cl.

| | |
|---|---|
| *F21V 33/00* | (2006.01) |
| *F21S 6/00* | (2006.01) |
| *F24F 6/14* | (2006.01) |
| *F21S 9/02* | (2006.01) |
| *F21Y 101/02* | (2006.01) |
| *F21W 121/00* | (2006.01) |

(52) U.S. Cl.
CPC .............. *F21V 33/0088* (2013.01); *F21S 6/001* (2013.01); *F21S 9/02* (2013.01); *F21V 33/0004* (2013.01); *F24F 6/14* (2013.01); *F21W 2121/00* (2013.01); *F21Y 2101/02* (2013.01)

(58) Field of Classification Search
CPC . F21Y 2101/02; A61L 2209/12; A61L 9/037; F21K 9/00

USPC ............................................................ 362/96
See application file for complete search history.

(56) References Cited

U.S. PATENT DOCUMENTS

| | | | | |
|---|---|---|---|---|
| 6,296,196 | B1 * | 10/2001 | Denen et al. ....................... | 239/4 |
| 6,446,880 | B1 * | 9/2002 | Schram et al. ................ | 239/145 |
| 2005/0169666 | A1 * | 8/2005 | Porchia et al. ................ | 399/111 |
| 2008/0315005 | A1 * | 12/2008 | Michaels et al. .................. | 239/4 |
| 2009/0009921 | A1 * | 1/2009 | Wosgien ....................... | 361/127 |
| 2013/0334336 | A1 * | 12/2013 | Haran et al. ....................... | 239/4 |

* cited by examiner

*Primary Examiner* — Sikha Roy
(74) *Attorney, Agent, or Firm* — Prakash Nama; Global IP Services, PLLC

(57) ABSTRACT

An LED candle lamp having the humidifying and flavoring function comprising a shell, a light emitting device mounted on the shell, a control system and a power supply unit, wherein the shell is provided inside with a humidifying device that includes a water storage tank, a sealing cover, an atomizing sheet and water absorbent cotton, the water storage tank and the sealing cover forming a sealed water storage space by being screwed together, the sealing cover being provided with an accommodating chamber provided inside with the atomizing sheet, the sealing cover being provided with a mist outlet exposed to the shell, the water storage tank being fixedly provided inside with the water absorbent cotton, wherein the control system may be a PCB control panel provided with an elastic contact conductive wire.

9 Claims, 10 Drawing Sheets

LED CANDLE LAMP HAVING HUMIDIFYING AND FLAVORING FUNCTION

BACKGROUND OF THE INVENTION

The present utility model relates to a candle lamp, particularly to an LED candle lamp having the humidifying and flavoring function.

With the continuous development of society, there is an ever increasing requirement of the life quality, with a candle lamp having become a main indoor decoration in various places. The current candle lamp is generally only used for lighting to render the scene atmosphere, having a single function, a complicated structure, low cost, and not so good practicality.

BRIEF SUMMARY OF THE INVENTION

In order to solve the above problem, the present utility model intends to provide a candle lamp, particularly an LED candle lamp having the humidifying and flavoring function.

In order to achieve the above purpose, the present utility model adopts the following technical solution: An LED candle lamp having the humidifying and flavoring function is provided, comprising a shell, a light emitting device mounted on the shell, a control system and a power supply unit, characterized in that: the shell is provided inside with a humidifying device that further includes a water storage tank, a sealing cover, an atomizing sheet and water absorbent cotton, the water storage tank and the sealing cover forming a sealed water storage space by being screwed together, the sealing cover being provided with a metal contact block and an accommodating chamber, the metal contact block being provided with an elastic contact spring, the sealing cover being provided with an accommodating chamber that is provided inside with the atomizing sheet, the sealing cover being provided with a mist outlet exposed to the shell, the water storage tank being fixedly provided inside with the water absorbent cotton, wherein the control system may be a PCB control panel provided with a conductive wire.

Besides, the light emitting device comprises a flame head and one or more LED lamps that can be disposed inside or outside the shell.

Besides, the humidifying device can be inserted into the shell from the top down or from the bottom up to be locked by snap connection.

Besides, the control system is disposed in the shell, and further comprises a spray control circuit and corresponding spray switch, a switch control circuit and corresponding power switch, a timing circuit and corresponding timing switch.

Besides, the power supply unit can be a battery box and a power battery pack, and is electrically connected to the control system.

Besides, the light emitting device includes a flame head and an LED lamp disposed in the flame head.

Besides, the atomizing sheet can be an ultrasonic atomizing sheet.

Besides, the shell can be provided coaxially either on its top or on its bottom with a mounting hole of the humidifying device.

Besides, there are at least one or more metal contact blocks.

Besides, the mist outlet can be disposed coaxially with the flame head, which is provided with a mist outlet slot.

Besides, the power supply unit can be connected with an external power supply through a power interface.

Besides, the water storage tank can be integrally formed together with the shell, and is provided with a cover exposed to the shell.

The present utility model has the following beneficial effects: The present utility model intends to provide an LED candle lamp having the humidifying and flavoring function which, with a humidifying device disposed on the candle, enables the candle lamp not only to project candlelight while in use through the simulation design, but also to humidify and flavor the air, so as to combine the functions of a humidifier and aromatherapy to make the environment more comfortable, having a simple structure, low cost, and good practicality.

LIST OF REFERENCE SIGNS

Figure 1:
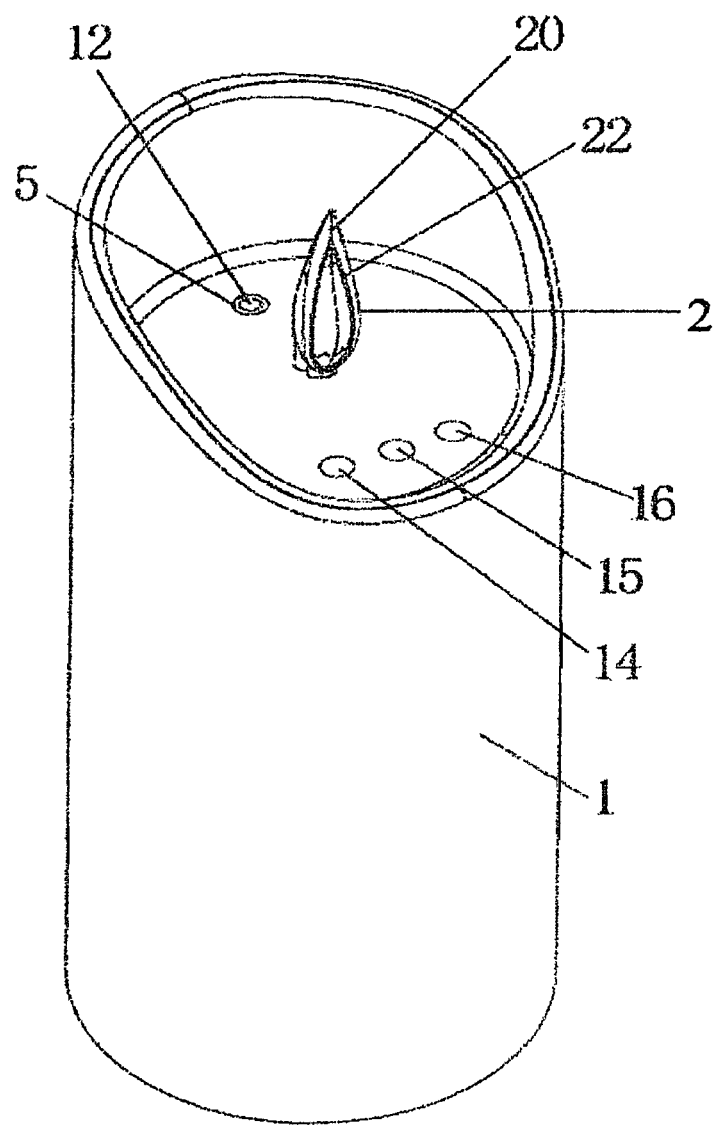
FIG. 1 is a schematic diagram of the overall structure of the present utility model.
Figure 2:
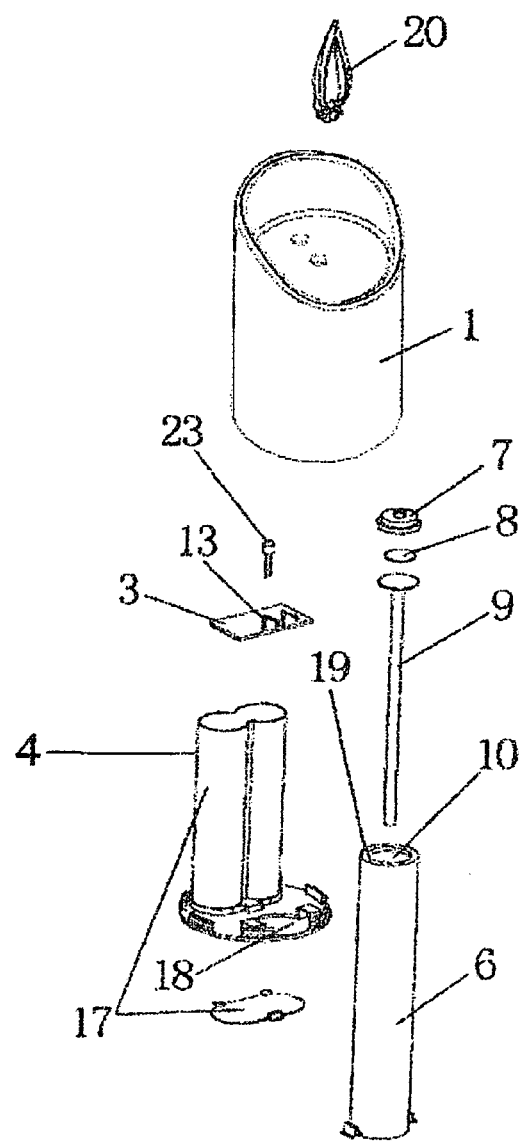
FIG. 2 is an exploded diagram of the overall structure of the present utility model.
Figure 3:
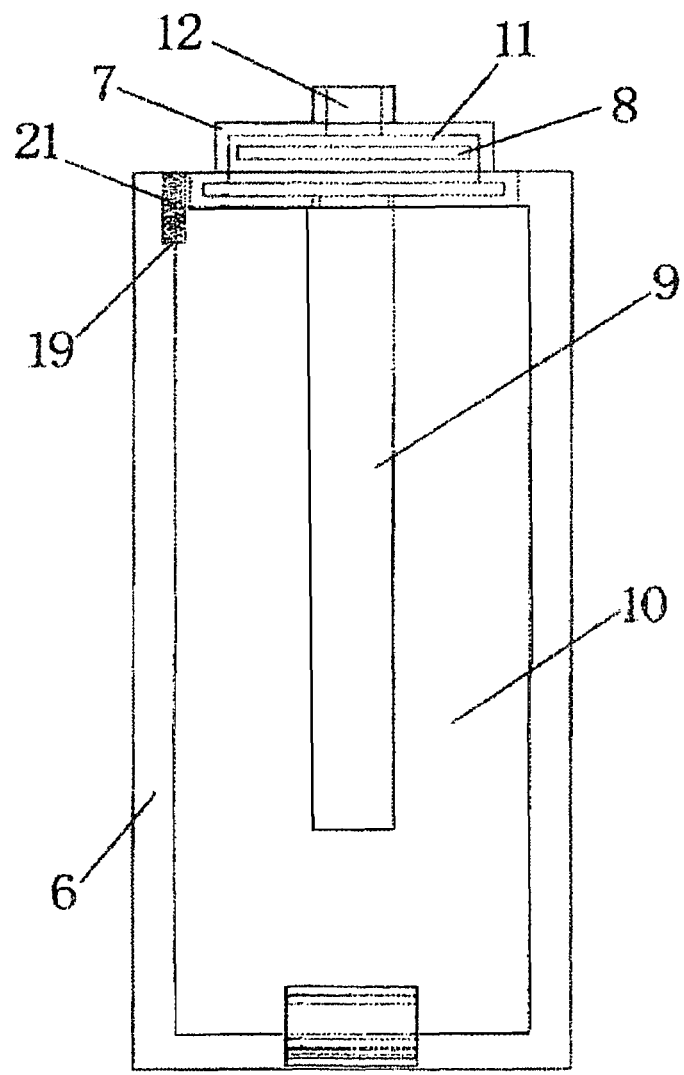
FIG. 3 is a perspective diagram of the humidifying device of the present utility model.

1. Shell; 2. light emitting device; 3. control system; 4. power supply unit; 5. humidifying device; 6. water storage tank; 7. sealing cover; 8. atomizing sheet; 9. water absorbent cotton; 10. water storage space; 11. accommodating chamber; 12. mist outlet; 13. wire; 14. spray switch; 15. power switch; 16. timing switch; 17. battery box; 18. mounting hole; 19. metal contact block; 20. flame head; 21. spring; 22. mist outlet slot; 23. LED lamp; 24. power interface; and 25. cover.

DETAILED DESCRIPTION OF THE INVENTION

The embodiments of the present utility model will be described in detail with reference to the drawings.

Example 1

As shown in FIGS. 1-7, an LED candle lamp having the humidifying and flavoring function is provided, comprising a shell 1, a light emitting device 2 mounted on the shell 1, a control system 3 and a power supply unit 4, characterized in that: the shell 1 is provided inside with a humidifying device 5 that further includes a water storage tank 6, a sealing cover 7, an atomizing sheet 8 and water absorbent cotton 9, the water storage tank 6 and the sealing cover 7 forming a sealed water storage space 10 by being screwed together, the sealing cover being provided with a metal contact block 19 and an accommodating chamber 11, the metal contact block 19 being provided with an elastic contact spring 21, the sealing cover 7 being provided with an accommodating chamber 11 that is provided inside with the atomizing sheet 8, the sealing cover 7 being provided with a mist outlet 12 exposed to the shell 1, the water storage tank 6 being fixedly provided inside with the water absorbent cotton 9, wherein the control system 3 may be a PCB control panel provided with a conductive wire 13.

Besides, the light emitting device 2 comprises a flame head 20 and one or more LED lamps 23 that can be disposed inside or outside the shell 1.

Besides, the humidifying device 5 can be inserted into the shell 1 from the top down or from the bottom up to be locked by snap connection.

Besides, the control system 3 is disposed in the shell 1, and further comprises a spray control circuit and corresponding spray switch 14, a switch control circuit and corresponding power switch 15, a timing circuit and corresponding timing switch 16.

Besides, the power supply unit 4 can be a battery box 17 and a power battery pack, and is electrically connected to the control system 3.

Besides, the light emitting device 2 includes a flame head 20 and an LED lamp disposed in the flame head 20.

Besides, the atomizing sheet 8 can be an ultrasonic atomizing sheet 8.

Besides, the shell 1 can be provided coaxially either on its top or on its bottom with a mounting hole 18 of the humidifying device 5.

Besides, there are at least one or more metal contact blocks 19.

Besides, the mist outlet 12 can be disposed coaxially with the flame head 20, which is provided with a mist outlet slot 22.

Besides, the power supply unit 4 can be connected with an external power supply through a power interface 24.

Besides, the water storage tank 6 can be integrally formed together with the shell 1, and is provided with a cover 25 exposed to the shell 1.

When the candle lamp of the present utility model needs to be used, first opening a battery cover on the bottom of the candle lamp and putting an adequate number of power batteries into the battery box 17, so as to be used as the power supply to supply power for each device of the candle lamp; unscrewing the sealing cover 7 of the humidifying device 5, and adding clear water onto the water storage tank 6 to wait for the liquid to be atomized; then screwing the sealing cover 7 and the water storage tank 6 tightly together, so as to prevent the liquid inside the water storage tank 6 from being leaked, while the water absorbent cotton 9 may absorb the clear water on the water storage tank 6 and send it to the atomizing zone; then the water storage tank 6, through the mounting hole 18 on the bottom, pushes the humidifying device 5 from the bottom up into the shell 1 of the candle lamp so as to secure it in place, during which the metal contact block 19 disposed on the sealing cover 7 of the humidifying device 5 may get into contact with the elastic conductive wire 13 on the control system 3, so that the elastic contact conductive wire 13 is deformed under pressure and thus stably placed against the metal contact block 19.

Next, turning on the power through the power switch 15 on the top of the shell 1 to turn on the LED lamp in the light emitting device 2, with the beam projected onto the flame head 20 to form the flame of the simulation candle; at the same time of turning on the power, the power supply unit 4 transfers electricity toward each device simultaneously, and the humidifying device 5 goes to standby; when the humidifying function needs to be used, the spray switch 14 is switched on, and then the liquid transferred up from the water absorbent cotton 9 is subject to ultrasonic atomizing treatment by the humidifying device 5 through the atomizing sheet 8, making the liquid on the water storage tank 6 atomized, with the mist sprayed out via the mist outlet 12 to humidify the environment; when continued humidifying is not needed, again touching the spray switch 14, and the continued spray humidifying can then be stopped.

Besides, with the timing switch 16 disposed on the shell 1, the candle lamp can be turned on or off regularly and the humidifying device 5 can be started regularly; when the candle lamp is not needed, the power switch 15 can be switched off by simply cutting off the power.

Example 2

Figure 4:
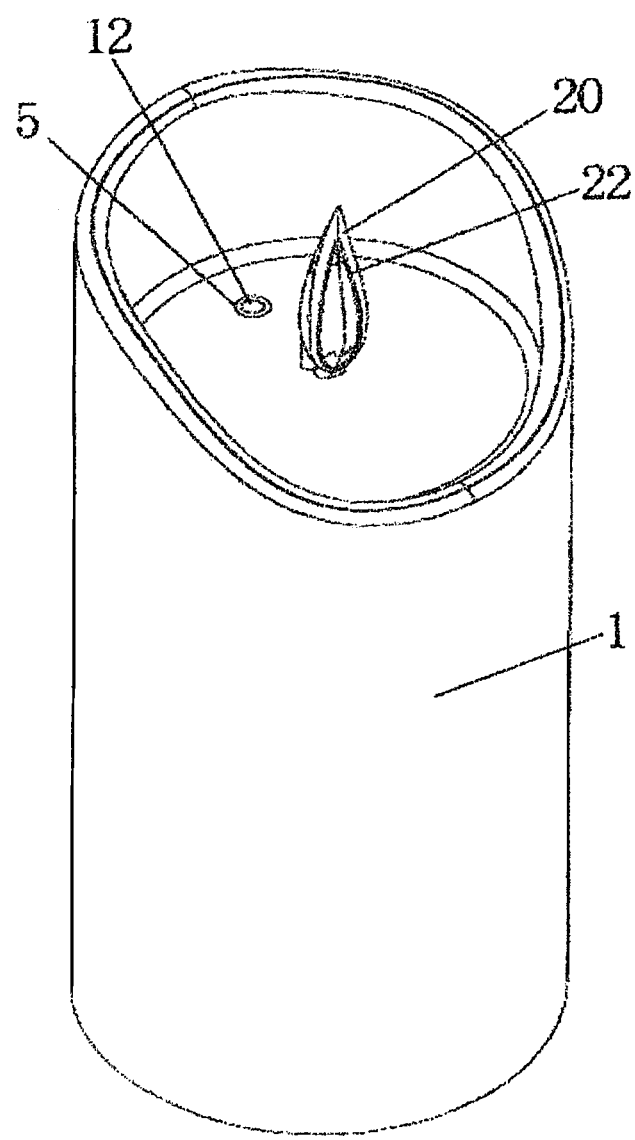
FIG. 4 is a schematic diagram of the overall structure of Example 2 of the present utility model.

As shown in FIG. 4, an LED candle lamp having the humidifying and flavoring function is provided, comprising a shell 1, a light emitting device 2 mounted on the shell 1, a control system 3 and a power supply unit 4, characterized in that: the shell 1 is provided inside with a humidifying device 5 that further includes a water storage tank 6, a sealing cover 7, an atomizing sheet 8 and water absorbent cotton 9, the water storage tank 6 and the sealing cover 7 forming a sealed water storage space 10 by being screwed together, the sealing cover being provided with a metal contact block 19 and an accommodating chamber 11, the metal contact block 19 being provided with an elastic contact spring 21, the sealing cover 7 being provided with an accommodating chamber 11 that is provided inside with the atomizing sheet 8, the sealing cover 7 being provided with a mist outlet 12 exposed to the shell 1, the water storage tank 6 being fixedly provided inside with the water absorbent cotton 9, wherein the control system 3 may be a PCB control panel provided with a conductive wire 13.

Besides, the light emitting device 2 comprises a flame head 20 and one or more LED lamps 23 that can be disposed inside or outside the shell 1.

Besides, the humidifying device 5 can be inserted into the shell 1 from the top down or from the bottom up to be locked by snap connection.

Besides, the control system 3 is disposed in the shell 1, and further comprises a spray control circuit and corresponding spray switch 14, a switch control circuit and corresponding power switch 15, a timing circuit and corresponding timing switch 16.

Besides, the power supply unit 4 can be a battery box 17 and a power battery pack, and is electrically connected to the control system 3.

Besides, the light emitting device 2 includes a flame head 20 and an LED lamp disposed in the flame head 20.

Besides, the atomizing sheet 8 can be an ultrasonic atomizing sheet 8.

Besides, the shell 1 can be provided coaxially either on its top or on its bottom with a mounting hole 18 of the humidifying device 5.

Besides, there are at least one or more metal contact blocks 19.

Besides, the mist outlet 12 can be disposed coaxially with the flame head 20, which is provided with a mist outlet slot 22.

Besides, the power supply unit 4 can be connected with an external power supply through a power interface 24.

Besides, the water storage tank 6 can be integrally formed together with the shell 1, and is provided with a cover 25 exposed to the shell 1.

When the candle lamp of the present utility model needs to be used, first opening a battery cover on the bottom of the candle lamp and putting an adequate number of power batteries into the battery box 17, so as to be used as the power supply to supply power for each device of the candle lamp; unscrewing the sealing cover 7 of the humidifying device 5, and adding clear water onto the water storage tank 6 to wait for the liquid to be atomized; then screwing the sealing cover 7 and the water storage tank 6 tightly together, so as to prevent the liquid inside the water storage tank 6 from being leaked, while the water absorbent cotton 9 may absorb the clear water on the water storage tank 6 and send it to the atomizing zone; then the water storage tank 6, through the mounting hole 18 on the bottom, pushes the humidifying device 5 from the bottom up into the shell 1 of the candle lamp so as to secure it in place, during which the metal contact block 19 disposed on the sealing cover 7 of the humidifying device 5 may get into contact with the elastic conductive wire 13 on the control system 3, so that the elastic contact conductive wire 13 is deformed under pressure and thus stably placed against the metal contact block 19.

Next, turning on the power through the power switch 15 on the bottom of the shell 1 to turn on the LED lamp in the light emitting device 2, with the beam projected onto the flame head 20 to form the flame of the simulation candle; at the same time of turning on the power, the power supply unit 4 transfers electricity toward each device simultaneously, and the humidifying device 5 goes to standby; when the humidifying function needs to be used, the spray switch 14 is switched on, and then the liquid transferred up from the water absorbent cotton 9 is subject to ultrasonic atomizing treatment by the humidifying device 5 through the atomizing sheet 8, making the liquid on the water storage tank 6 atomized, with the mist sprayed out via the mist outlet 12 to humidify the environment; when continued humidifying is not needed, again touching the spray switch 14, and the continued spray humidifying can then be stopped.

Besides, with the timing switch 16 disposed on the shell 1, the candle lamp can be turned on or off regularly and the humidifying device 5 can be started regularly; when the candle lamp is not needed, the power switch 15 can be switched off by simply cutting off the power.

Example 3

Figure 5:
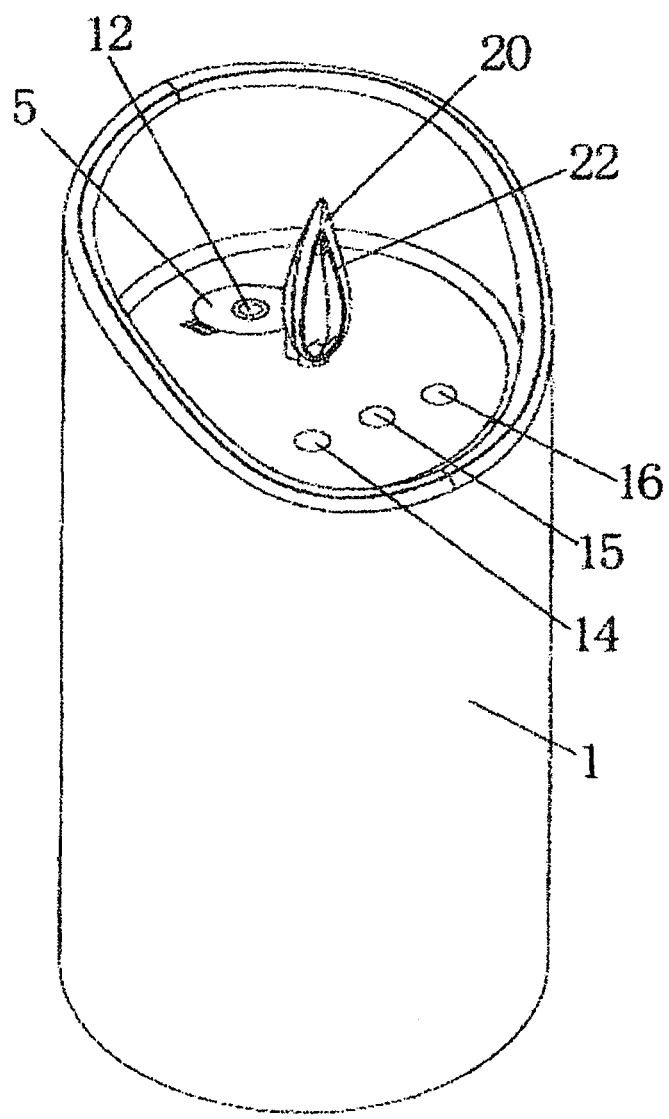
FIG. 5 is a schematic diagram of the overall structure of Example 3 of the present utility model.

As shown in FIG. 5, an LED candle lamp having the humidifying and flavoring function is provided, comprising a shell 1, a light emitting device 2 mounted on the shell 1, a control system 3 and a power supply unit 4, characterized in that: the shell 1 is provided inside with a humidifying device 5 that further includes a water storage tank 6, a sealing cover 7, an atomizing sheet 8 and water absorbent cotton 9, the water storage tank 6 and the sealing cover 7 forming a sealed water storage space 10 by being screwed together, the sealing cover being provided with a metal contact block 19 and an accommodating chamber 11, the metal contact block 19 being provided with an elastic contact spring 21, the sealing cover 7 being provided with an accommodating chamber 11 that is provided inside with the atomizing sheet 8, the sealing cover 7 being provided with a mist outlet 12 exposed to the shell 1, the water storage tank 6 being fixedly provided inside with the water absorbent cotton 9, wherein the control system 3 may be a PCB control panel provided with a conductive wire 13.

Besides, the light emitting device 2 comprises a flame head 20 and one or more LED lamps 23 that can be disposed inside or outside the shell 1.

Besides, the humidifying device 5 can be inserted into the shell 1 from the top down or from the bottom up to be locked by snap connection.

Besides, the control system 3 is disposed in the shell 1, and further comprises a spray control circuit and corresponding spray switch 14, a switch control circuit and corresponding power switch 15, a timing circuit and corresponding timing switch 16.

Besides, the power supply unit 4 can be a battery box 17 and a power battery pack, and is electrically connected to the control system 3.

Besides, the light emitting device 2 includes a flame head 20 and an LED lamp disposed in the flame head 20.

Besides, the atomizing sheet 8 can be an ultrasonic atomizing sheet 8.

Besides, the shell 1 can be provided coaxially either on its top or on its bottom with a mounting hole 18 of the humidifying device 5.

Besides, there are at least one or more metal contact blocks 19.

Besides, the mist outlet 12 can be disposed coaxially with the flame head 20, which is provided with a mist outlet slot 22.

Besides, the power supply unit 4 can be connected with an external power supply through a power interface 24.

Besides, the water storage tank 6 can be integrally formed together with the shell 1, and is provided with a cover 25 exposed to the shell 1.

When the candle lamp of the present utility model needs to be used, first opening a battery cover on the bottom of the candle lamp and putting an adequate number of power batteries into the battery box 17, so as to be used as the power supply to supply power for each device of the candle lamp; unscrewing the sealing cover 7 of the humidifying device 5, and adding clear water onto the water storage tank 6 to wait for the liquid to be atomized; then screwing the sealing cover 7 and the water storage tank 6 tightly together, so as to prevent the liquid inside the water storage tank 6 from being leaked, while the water absorbent cotton 9 may absorb the clear water on the water storage tank 6 and send it to the atomizing zone; then the water storage tank 6, through the mounting hole 18 on the top, pushes the humidifying device 5 from the top down into the shell 1 of the candle lamp so as to secure it in place, during which the metal contact block 19 disposed on the sealing cover 7 of the humidifying device 5 may get into contact with the elastic conductive wire 13 on the control system 3, so that the elastic contact conductive wire 13 is deformed under pressure and thus stably placed against the metal contact block 19.

Next, turning on the power through the power switch 15 on the top of the shell 1 to turn on the LED lamp in the light emitting device 2, with the beam projected onto the flame head 20 to form the flame of the simulation candle; at the same time of turning on the power, the power supply unit 4 transfers electricity toward each device simultaneously, and the humidifying device 5 goes to standby; when the humidifying function needs to be used, the spray switch 14 is switched on, and then the liquid transferred up from the water absorbent cotton 9 is subject to ultrasonic atomizing treatment by the humidifying device 5 through the atomizing sheet 8, making the liquid on the water storage tank 6 atomized, with the mist sprayed out via the mist outlet 12 to humidify the environment; when continued humidifying is not needed, again touching the spray switch 14, and the continued spray humidifying can then be stopped.

Besides, with the timing switch 16 disposed on the shell 1, the candle lamp can be turned on or off regularly and the humidifying device 5 can be started regularly; when the candle lamp is not needed, the power switch 15 can be switched off by simply cutting off the power.

Example 4

Figure 6:
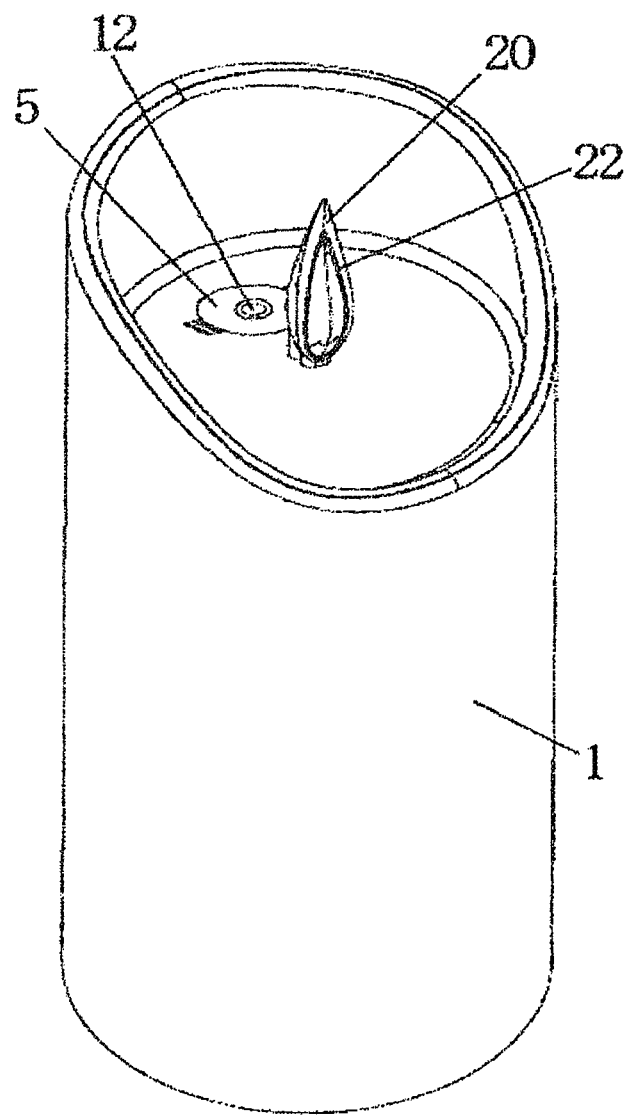
FIG. 6 is a schematic diagram of the overall structure of Example 4 of the present utility model.
Figure 7:
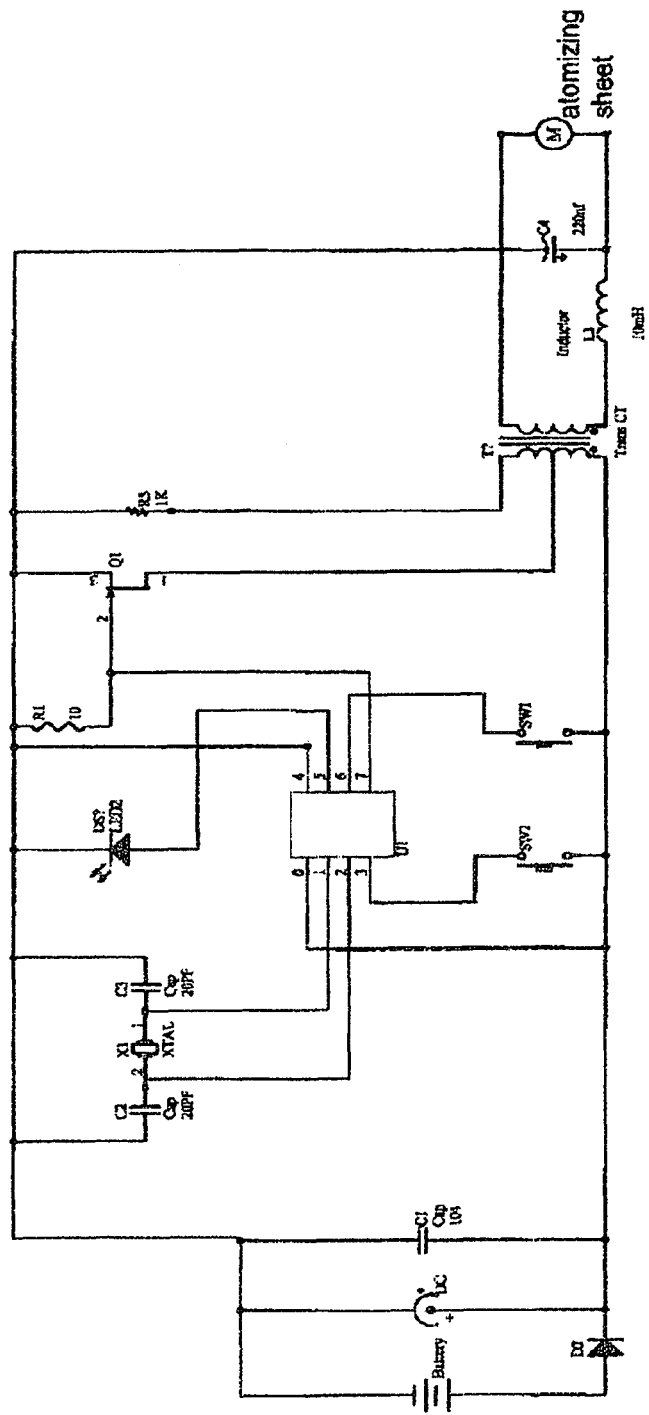
FIG. 7 is an electrical principle diagram of the present utility model.
Figure 8:
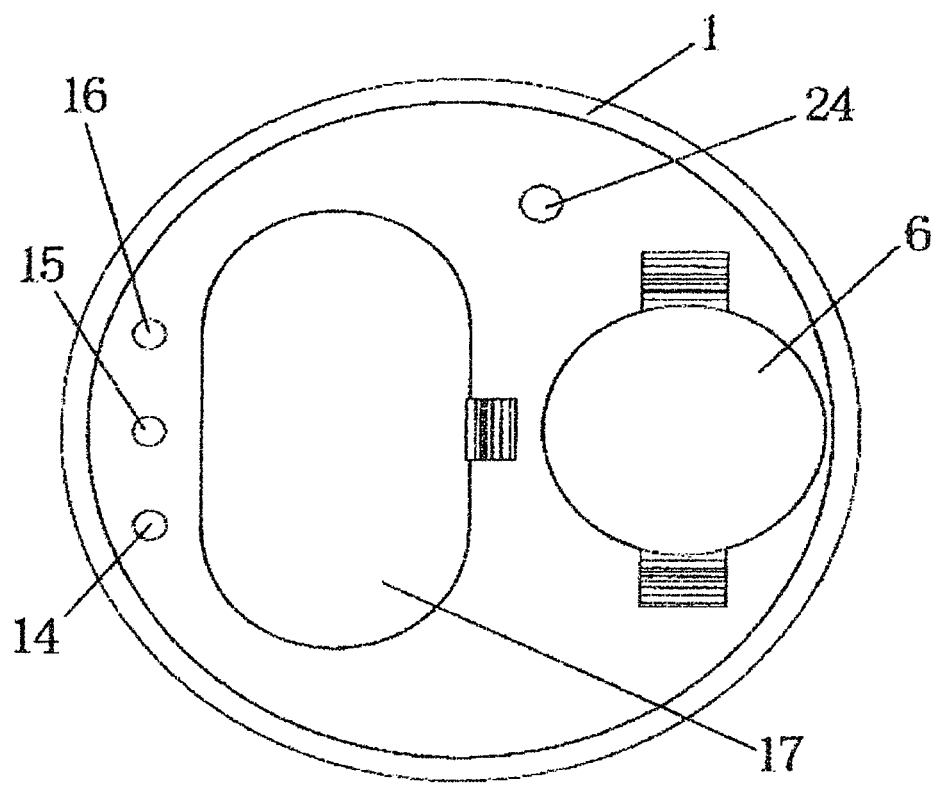
FIG. 8 is a structural schematic diagram when the present utility model is provided on its bottom with a button.
Figure 9:
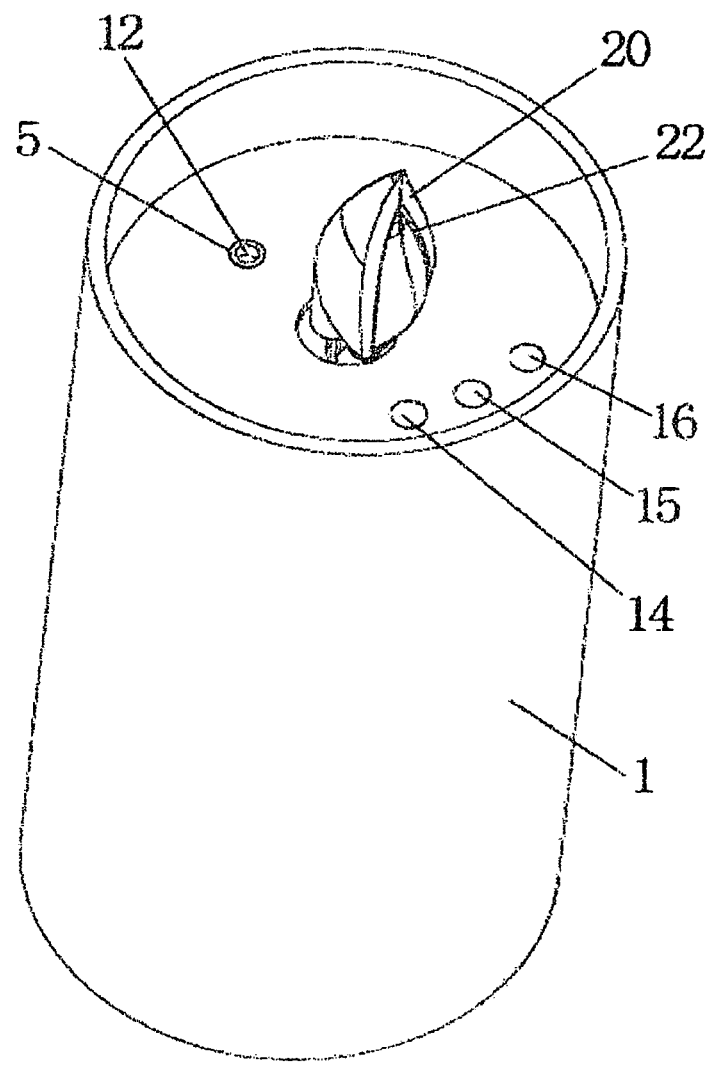
FIG. 9 is a structural schematic diagram when the shell of the present utility model is cylindrical.
Figure 10:
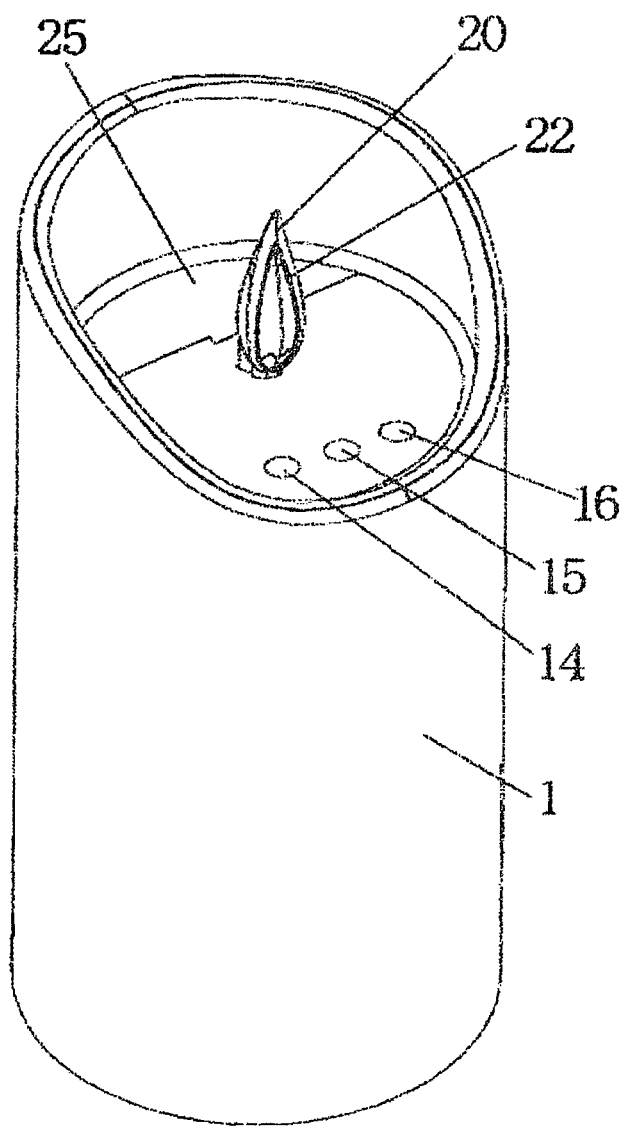
FIG. 10 is a structural schematic diagram of the cover-type water storage tank of the present utility model.

As shown in FIG. 6, an LED candle lamp having the humidifying and flavoring function is provided, comprising a shell 1, a light emitting device 2 mounted on the shell 1, a control system 3 and a power supply unit 4, characterized in that: the shell 1 is provided inside with a humidifying device 5 that further includes a water storage tank 6, a sealing cover 7, an atomizing sheet 8 and water absorbent cotton 9, the water storage tank 6 and the sealing cover 7 forming a sealed water storage space 10 by being screwed together, the sealing cover being provided with a metal contact block 19 and an accommodating chamber 11, the metal contact block 19 being provided with an elastic contact spring 21, the sealing cover 7 being provided with an accommodating chamber 11 that is provided inside with the atomizing sheet 8, the sealing cover 7 being provided with a mist outlet 12 exposed to the shell 1, the water storage tank 6 being fixedly provided inside with the water absorbent cotton 9, wherein the control system 3 may be a PCB control panel provided with a conductive wire 13.

Besides, the light emitting device 2 comprises a flame head 20 and one or more LED lamps 23 that can be disposed inside or outside the shell 1.

Besides, the humidifying device 5 can be inserted into the shell 1 from the top down or from the bottom up to be locked by snap connection.

Besides, the control system 3 is disposed in the shell 1, and further comprises a spray control circuit and corresponding spray switch 14, a switch control circuit and corresponding power switch 15, a timing circuit and corresponding timing switch 16.

Besides, the power supply unit 4 can be a battery box 17 and a power battery pack, and is electrically connected to the control system 3.

Besides, the light emitting device 2 includes a flame head 20 and an LED lamp disposed in the flame head 20.

Besides, the atomizing sheet 8 can be an ultrasonic atomizing sheet 8.

Besides, the shell 1 can be provided coaxially either on its top or on its bottom with a mounting hole 18 of the humidifying device 5.

Besides, there are at least one or more metal contact blocks 19.

Besides, the mist outlet 12 can be disposed coaxially with the flame head 20, which is provided with a mist outlet slot 22.

Besides, the power supply unit 4 can be connected with an external power supply through a power interface 24.

Besides, the water storage tank 6 can be integrally formed together with the shell 1, and is provided with a cover 25 exposed to the shell 1.

When the candle lamp of the present utility model needs to be used, first opening a battery cover on the bottom of the candle lamp and putting an adequate number of power batteries into the battery box 17, so as to be used as the power supply to supply power for each device of the candle lamp; unscrewing the sealing cover 7 of the humidifying device 5, and adding clear water onto the water storage tank 6 to wait for the liquid to be atomized; then screwing the sealing cover 7 and the water storage tank 6 tightly together, so as to prevent the liquid inside the water storage tank 6 from being leaked, while the water absorbent cotton 9 may absorb the clear water on the water storage tank 6 and send it to the atomizing zone; then the water storage tank 6, through the mounting hole 18 on the top, pushes the humidifying device 5 from the top down into the shell 1 of the candle lamp so as to secure it in place, during which the metal contact block 19 disposed on the sealing cover 7 of the humidifying device 5 may get into contact with the elastic conductive wire 13 on the control system 3, so that the elastic contact conductive wire 13 is deformed under pressure and thus stably placed against the metal contact block 19.

Next, turning on the power through the power switch 15 on the bottom of the shell 1 to turn on the LED lamp in the light emitting device 2, with the beam projected onto the flame head 20 to form the flame of the simulation candle; at the same time of turning on the power, the power supply unit 4 transfers electricity toward each device simultaneously, and the humidifying device 5 goes to standby; when the humidifying function needs to be used, the spray switch 14 is switched on, and then the liquid transferred up from the water absorbent cotton 9 is subject to ultrasonic atomizing treatment by the humidifying device 5 through the atomizing sheet 8, making the liquid on the water storage tank 6 atomized, with the mist sprayed out via the mist outlet 12 to humidify the environment; when continued humidifying is not needed, again touching the spray switch 14, and the continued spray humidifying can then be stopped.

Besides, with the timing switch 16 disposed on the shell 1, the candle lamp can be turned on or off regularly and the humidifying device 5 can be started regularly; when the candle lamp is not needed, the power switch 15 can be switched off by simply cutting off the power.

The above examples are just preferred examples of the present utility model, rather than any restriction of the technical scope of the present utility model. Those skilled in the art, under the inspiration of the technical solution of the present utility model, can make some deformation and amendment, with any amendment, equivalent change and modification made on the above examples based on the technical substance of the present utility model falling within the scope of the technical solution of the present utility model.

What is claimed is:

1. An LED candle lamp having a humidifying and flavoring function, comprising a shell, a light emitting device mounted on the shell, a control system and a power supply unit, characterized in that: the shell is provided inside with a humidifying device that further includes a water storage tank, a sealing cover, an atomizing sheet and water absorbent cotton, the water storage tank and the sealing cover forming a seated water storage space by being screwed together, the sealing cover being provided with a metal contact block and an accommodating chamber, the metal contact block being provided with an elastic contact spring, the accommodating chamber being provided inside with the atomizing sheet, the sealing cover being provided with a mist outlet exposed to the shell, the water storage tank being fixedly provided inside with the water absorbent cotton, wherein the control system is a PCB control panel provided with a conductive wire; the light emitting device comprises a flame head and one or more LED lamps being disposed inside or outside the shell; the mist outlet is disposed coaxially with the flame head, which is provided with a mist outlet slot.

2. The LED candle lamp having the humidifying and flavoring function according to claim 1, characterized in that: the humidifying device is inserted into the shell according to a top-down direction or a bottom-up direction to be locked by snap connection.

3. The LED candle lamp having the humidifying and flavoring function according to claim 1, characterized in that: the control system is disposed in the shell, and further comprises a spray control circuit and a corresponding spray switch, a switch control circuit and a corresponding power switch, a timing circuit and corresponding timing switch.

4. The LED candle lamp having the humidifying and flavoring function according to claim 1, characterized in that the power supply unit is a battery box and a power battery pack, and is electrically connected to the control system.

5. The LED candle lamp having the humidifying and flavoring function according to claim 1, characterized in that: the atomizing sheet is an ultrasonic atomizing sheet.

6. The LED candle lamp having the humidifying and flavoring function according to claim 1, characterized in that: the shell is provided coaxially either on its top or on its bottom with a mounting hole of the humidifying device.

7. The LED candle lamp having the humidifying and flavoring function according to claim 1, characterized in that: the sealing cover is provided with additional metal contact blocks.

8. The LED candle lamp having the humidifying and flavoring function according to claim 1, characterized in that: the power supply unit is connected with an external power supply through a power interface.

9. The LED candle lamp having the humidifying and flavoring function according to claim 1, characterized in that: the water storage tank is integrally formed together with the shell, and is provided with a cover exposed to the shell.

* * * * *